(12) United States Patent
Lassalas et al.

(10) Patent No.: US 11,432,963 B2
(45) Date of Patent: Sep. 6, 2022

(54) ALIGNING MULTI-WAVELENGTH LASER BEAMS WITH CORES OF A MULTI-CORE FIBER

(71) Applicant: Alcon Inc., Fribourg (CH)

(72) Inventors: Bruno Lassalas, Foothill Ranch, CA (US); Mark Harrison Farley, Laguna Hills, CA (US); Alireza Mirsepassi, Irvine, CA (US); Ronald T. Smith, Irvine, CA (US)

(73) Assignee: Alcon Inc., Fribourg (CH)

(*) Notice: Subject to any disclaimer, the term of this patent is extended or adjusted under 35 U.S.C. 154(b) by 134 days.

(21) Appl. No.: 16/884,262

(22) Filed: May 27, 2020

(65) Prior Publication Data

US 2020/0375660 A1 Dec. 3, 2020

Related U.S. Application Data

(60) Provisional application No. 62/856,377, filed on Jun. 3, 2019.

(51) Int. Cl.
*A61F 9/008* (2006.01)
*A61B 18/22* (2006.01)
*A61B 18/20* (2006.01)

(52) U.S. Cl.
CPC .......... *A61F 9/00823* (2013.01); *A61B 18/22* (2013.01); *A61B 2018/207* (2013.01); *A61B 2018/2211* (2013.01); *A61B 2018/2272* (2013.01); *A61B 2018/2294* (2013.01); *A61F 2009/00863* (2013.01)

(58) Field of Classification Search
CPC ............ A61F 9/008; A61B 18/20; A61N 5/06
See application file for complete search history.

(56) References Cited

U.S. PATENT DOCUMENTS

| | | | |
|---|---|---|---|
| 5,139,494 A | * | 8/1992 | Freiberg ................ A61B 18/24 606/15 |
| 6,078,708 A | | 6/2000 | De La Tocnay |
| 7,566,173 B2 | | 7/2009 | Auld et al. |
| 8,262,647 B2 | | 9/2012 | Raksi |
| 8,267,925 B2 | | 9/2012 | Raksi |
| 8,561,280 B2 | | 10/2013 | Diao et al. |
| 8,679,100 B2 | | 3/2014 | Raksi |

(Continued)

FOREIGN PATENT DOCUMENTS

JP  5831403 B2  11/2015
WO  2018037362 A1  3/2018

*Primary Examiner* — Lynsey C Eiseman

(57) ABSTRACT

Particular embodiments disclosed herein provide a surgical laser system comprising first laser source configured to emit a first laser beam with a first wavelength and a second laser source configured to emit a second laser beam with a second wavelength. The surgical laser system further comprises a first diffraction optical element (DOE) tuned to the first wavelength and a second DOE tuned to the second wavelength, wherein the first DOE is configured to diffract the first laser beam into one or more first diffracted beams at a diffraction angle and the second DOE is configured to diffract the second laser beam into one or more second diffracted beams at the same diffraction angle. The surgical laser system further comprises one or more beam splitters configured to reflect the one or more first diffracted beams and the one or more second diffracted beams onto a lens.

3 Claims, 6 Drawing Sheets

(56) References Cited

U.S. PATENT DOCUMENTS

| | | |
|---|---|---|
| 8,764,261 B2 | 7/2014 | Smith |
| 8,951,244 B2 | 2/2015 | Smith |
| 9,308,128 B2 | 4/2016 | Smith |
| 9,504,608 B2 | 11/2016 | Raksi |
| 10,245,181 B2 | 4/2019 | Diao |
| 10,507,074 B2 | 12/2019 | Smith |
| 10,639,198 B2 | 5/2020 | Farley |
| 2006/0170867 A1* | 8/2006 | Koschmieder .......... A61F 9/008 351/205 |
| 2007/0265602 A1* | 11/2007 | Mordaunt ............... A61F 9/008 606/4 |
| 2008/0243108 A1 | 10/2008 | Murakami |
| 2009/0015923 A1 | 1/2009 | Auld |
| 2013/0150839 A1* | 6/2013 | Smith ................. A61F 9/00821 606/4 |
| 2014/0200566 A1 | 7/2014 | Smith |
| 2016/0082294 A1* | 3/2016 | Luttrull ............... A61N 5/0603 601/3 |
| 2018/0243136 A1 | 8/2018 | Diao |
| 2019/0142544 A1 | 5/2019 | Horn |
| 2019/0175300 A1* | 6/2019 | Horn .................. A61F 9/00823 |
| 2019/0175405 A1 | 6/2019 | Diao |
| 2019/0175407 A1 | 6/2019 | Bacher |

\* cited by examiner

ALIGNING MULTI-WAVELENGTH LASER BEAMS WITH CORES OF A MULTI-CORE FIBER

PRIORITY CLAIM

This application claims the benefit of priority of U.S. Provisional Patent Application Ser. No. 62/856,377 titled "Aligning Multi-Wavelength Laser Beams with Cores of a Multi-Core Fiber", filed on Jun. 3, 2019, whose inventors are Bruno Lassalas, Mark Harrison Farley, Alireza Mirsepassi, and Ronald T. Smith, which is hereby incorporated by reference in its entirety as though fully and completely set forth herein.

TECHNICAL FIELD

The present disclosure relates generally to a surgical laser system and more specifically to configuring a surgical laser system to align multi-wavelength laser beams with the cores of a multi-core fiber.

BACKGROUND

In a wide variety of medical procedures, laser light (e.g., a illumination beam, laser treatment beam ("treatment beam"), and/or laser aiming beam ("aiming beam")) is used to assist in surgery and/or treat patient anatomy. For example, in laser photocoagulation, a laser probe propagates a treatment beam to cauterize blood vessels at a laser burn spot across the retina. A treatment beam is typically transmitted from a surgical laser system through an optical fiber cable that proximally terminates in a port adapter, which connects to the surgical laser system, and distally terminates in the laser probe, which is manipulated by the surgeon. Note that, herein, a distal end of a component refers to the end that is closer to a patient's body while the proximal end of the component refers to the end that is facing away from the patient's body or in proximity to, for example, the surgical laser system.

In addition to cauterizing blood vessels at the laser burn spot, the treatment beam may also damage some of the rods and cones that are present in the retina that provide vision, thereby, affecting eyesight. Since vision is most acute at the central macula of the retina, the surgeon arranges the laser probe to generate a laser burn spot in the peripheral areas of the retina. During the procedure, the surgeon drives the probe with a non-burning aiming beam to illuminate the retinal area that is to be photocoagulated. Due to the availability of low-power red laser diodes, the aiming beam is generally a low-power red laser light. Once the surgeon has positioned the laser probe so as to illuminate a desired retinal spot with the aiming beam, the surgeon activates the treatment beam, through a foot pedal or other means, to photocoagulate the illuminated area (or an area encompassing the illuminated area) using the treatment beam. Having burned a retinal spot, the surgeon repositions the probe to illuminate a new spot with the aiming light, activates the treatment beam to photocoagulate the new spot, repositions the probe, and so on until a desired number of burned laser spots are distributed across the retina.

Certain types of laser probes coagulate or burn multiple spots at a time, which may result in a faster and more efficient photocoagulation. For example, a surgical laser system that is coupled to one of such laser probes through an optical fiber may be configured to split a single laser beam into multiple laser beams that exhibit a laser spot pattern. In such an example, the surgical laser system transmits the multiple laser beams to the optical cable, which may include an array of multiple optical fibers or a multi-core fiber that exhibit a corresponding fiber pattern.

For diabetic retinopathy, a pan-retinal photocoagulation (PRP) procedure may be conducted, and the number of required laser photocoagulations for PRP is typically large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot/multi-fiber laser probes have been developed and described in U.S. Pat. Nos. 8,951,244 and 8,561,280 as well as U.S. application Ser. No. 16/218,333. In addition to the aiming beam and the treatment beam, vitreoretinal procedures also benefit from illumination light or beam being directed into the eye and onto retinal tissue.

BRIEF SUMMARY

The present disclosure relates generally to a surgical laser system and more specifically to configuring a surgical laser system to align multi-wavelength laser beams with the cores of a multi-core fiber.

Certain embodiments of the present disclosure provide a surgical laser system comprising a first laser source configured to emit a first laser beam with a first wavelength and a second laser source configured to emit a second laser beam with a second wavelength. The surgical laser system further comprises a first diffraction optical element (DOE) tuned to the first wavelength and a second DOE tuned to the second wavelength, wherein the first DOE is configured to diffract the first laser beam into one or more first diffracted beams at a diffraction angle and the second DOE is configured to diffract the second laser beam into one or more second diffracted beams at the same diffraction angle. The surgical laser system further comprises one or more beam splitters configured to reflect the one or more first diffracted beams and the one or more second diffracted beams onto a lens. The lens is configured to focus the one or more first diffracted beams and the one or more second diffracted beams onto an interface plane of a proximal end of a cable coupled to the surgical laser system, wherein a distal end of the cable is configured to emit the one or more first diffracted beams and the one or more second diffracted beams onto a target surface.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a surgical laser system configured to align multi-wavelength laser beams with the cores of a multi-core fiber.

Figure 1:
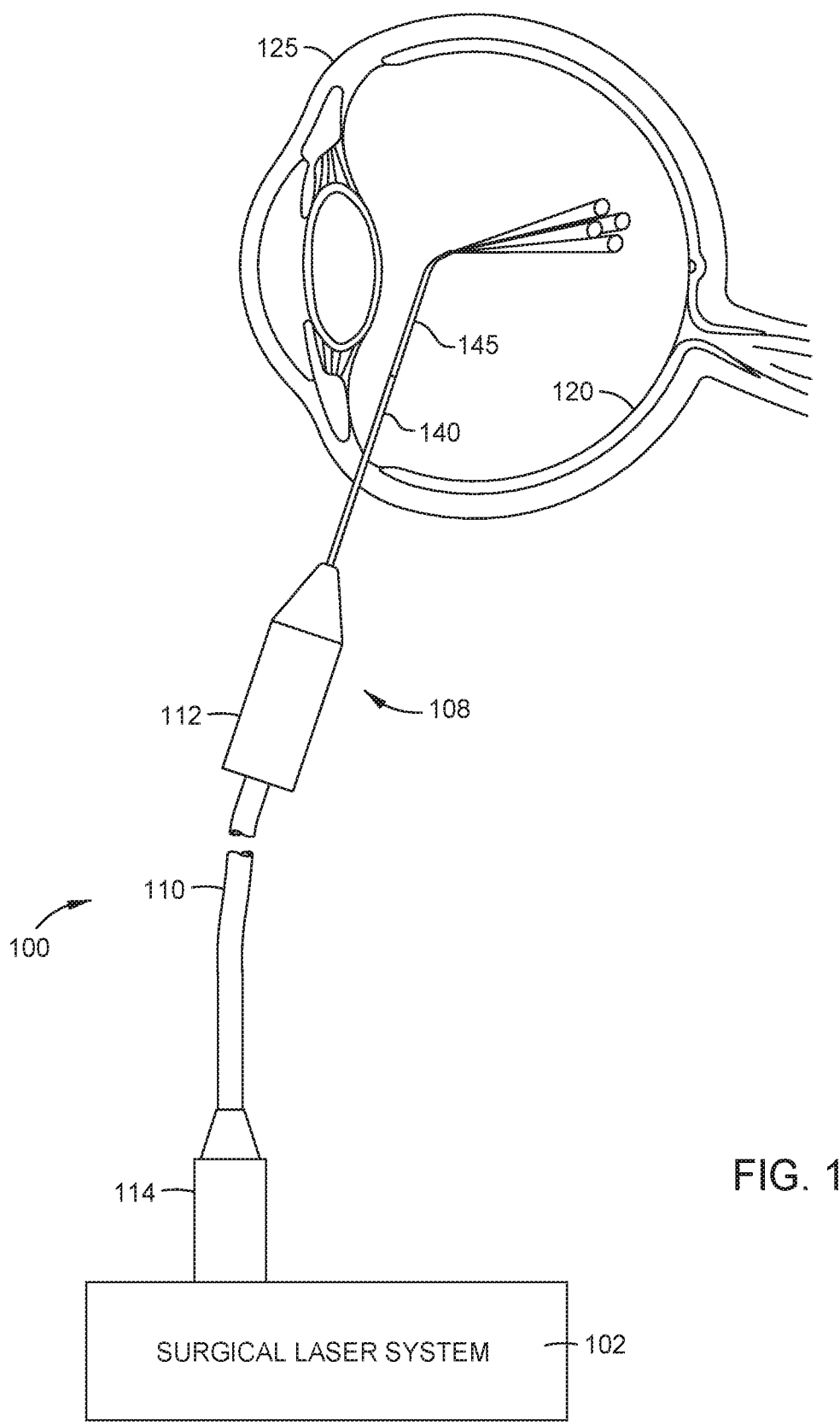
FIG. 1 illustrates an example system for creating a multi-spot pattern of laser beams, in accordance with certain aspects of the present disclosure.

FIG. 1 illustrates an example system 100 for creating a multi-spot pattern of laser beams on the surface of the retina, according to certain embodiments of the present invention. System 100 includes a surgical laser system 102 having one or more laser sources for generating laser beams used during ophthalmic procedures. For example, a first laser source within surgical laser system 102 may generate a treatment beam with a first wavelength (e.g., ~532 nanometers (nm)) while a second laser source may generate an aiming beam with a second wavelength (e.g., ~635 nm). A user, such as a surgeon, may trigger the surgical laser system 102 (e.g., via a foot switch, voice commands, etc.) to emit the aiming beam onto a desired retinal spot. Once the surgeon has positioned the laser probe so as to illuminate the desired retinal spot with the aiming beam, the surgeon activates the treatment beam, such as through a foot pedal or other means, to treat the targeted patient anatomy (e.g., photocoagulate the desired retinal spot using the treatment beam).

As shown, surgical laser system 102 includes a connector or port adapter 114 that couples to an optical port (not shown) of surgical laser system 102. FIG. 1 also shows a cable 110 having a distal end that couples to and extends through a probe 108 and a proximal end that couples to and extends through port adapter 114. In the example of FIG. 1, port adapter 114 includes a ferrule with an opening that allows laser beams from surgical laser system 102 to be propagated into an interface plane (also referred to as a proximal entrance plane) of the proximal end of cable 110. The interface plane of cable 110 comprises the exposed proximal ends of the one or more cores where laser beams may be directed to. In the example of FIG. 1, cable 110 is a multi-core optical fiber cable (MCF) with four cores. As such, the interface plane of the proximal end of cable 110 comprises the proximal ends of the four cores that are exposed through the opening of the ferrule of port adapter 114.

Surgical laser system 102 may be configured to split a single laser beam that is generated by a laser source into multiple laser beams that exhibit a laser spot pattern. For example, surgical laser system 102 may split a single aiming beam into four aiming beams and then deliver the four aiming beams to the interface plane of cable 110 through the opening of the ferrule of port adapter 114. Surgical laser system 102 may further be configured to split a single treatment beam into four treatment beams and deliver the four treatment beams to the interface plane of cable 110 through the opening of the ferrule. In such an example, each of the cores of cable 110 would then be transmitting both an aiming beam and a treatment beam, which may be referred to, collectively, as a combined beam or a multi-wavelength beam (due to the fact that the aiming beam and treatment beam have different wavelengths). In some examples, surgical laser system 102 may also propagate an illumination beam into an interface plane of cable 110 (e.g., which may also include a proximal end of a cladding that holds the cores within cable 110) in order to illuminate the inside of the eye, especially areas of the retina 120 that are to be photocoagulated. In certain aspects, an illumination beam may be generated by a white light-emitting diode (LED).

Cable 110 delivers the combined beams to probe 108, which propagates a multi-spot pattern (e.g., four spots) of combined beams to the retina 120 of a patient's eye 125. Probe 108 includes a probe body 112 at its proximal end and a probe tip 140 at its distal end. Probe body 112 and probe tip 140 house and protect the distal end of cable 110. A distal end portion 145 of the probe tip 140 may also contain a lens that focuses the combined beams on the retina 120.

Figure 2:
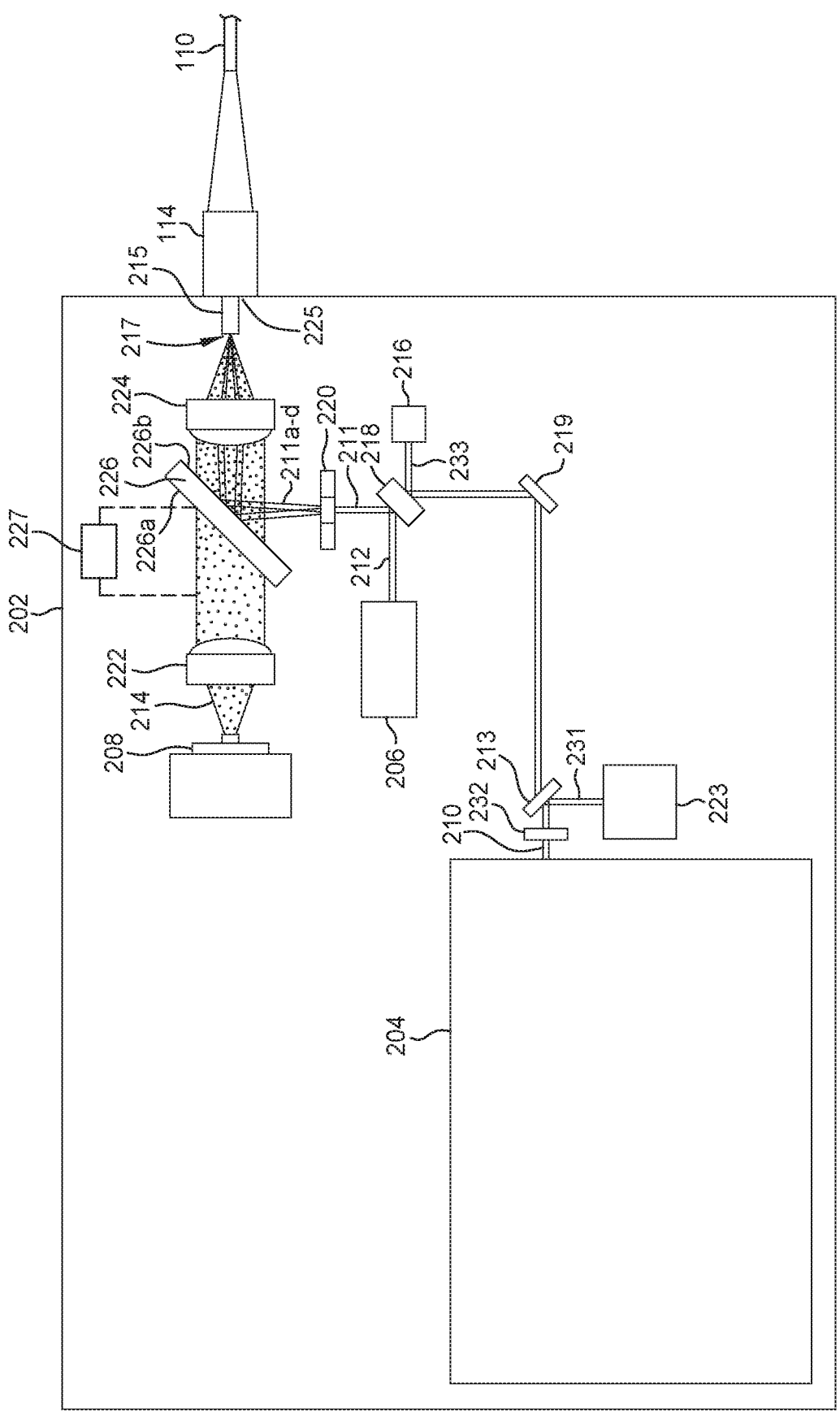
FIG. 2 illustrates an example of a surgical laser system, and the components therein, used for creating a multi-spot pattern of laser beams, in accordance with certain aspects of the present disclosure.

Various systems can be employed to create a multi-spot pattern of combined laser beams. FIG. 2 illustrates one example of a surgical laser system, and the components therein, that may be used for creating a multi-spot pattern of combined laser beams. Surgical laser system 202 comprises a laser source 204, which generates a treatment beam 210, a laser source 206, which generates an aiming beam 212, and a light source 208, which generates an illumination beam 214.

At the outset of the surgery, a surgeon may activate light source 208 in order to illuminate the inside of the eye's globe and make it easier to view the retina. As shown, once emitted by light source 208, illumination beam 214 is received by collimating lens 222, which is configured to produce a beam with parallel (collimated) rays of light. In certain embodiments, collimating lens 222 may be a multi-element achromat comprising two singlet lenses and one doublet lens. Therefore, as shown, illumination beam 214 emerges with parallel rays of light from the other side of collimating lens 222 and passes through beam splitter 226 to reach a condensing lens 224. In certain embodiments, condensing lens 224 may be a multi-element achromat comprising two singlet lenses and one doublet lens. In embodiments, condensing lens 224 has the same exact design as collimating lens 222, except that the assembly is revered (e.g., rotated by 180 degrees), thereby creating a one-to-one magnification imaging system. Beam splitter 226 may have different coatings on its two sides, 226a and 226b. For example, side 226a is coated such that it allows light propagated thereon to pass through beam splitter 226. As such, illumination beam 214, which is propagated onto side 226a passes beam splitter 226. On the other hand, side 226b is coated to reflect light or laser beams such as treatment beam 210 and aiming beam 212, as further described below. Although, note that a trivial portion of illumination beam 214 is reflected by side 226a onto sensor 227, which is configured to sense illumination beam 214.

Condensing lens 224 then converges illumination beam 214 into an interface plane of a proximal end of a cable, such as cable 110 shown in FIG. 1, that is coupled to a port 225 of surgical laser system 202 through port adapter 114. As described in relation to FIG. 1, cable 110 is a cable with four cores. As such, condensing lens 224 focuses illumination beam 214 into an interface plane of cable 110 such that illumination beam 214 is propagated, along an entire length of each of the four cores of cable 110, to the distal end of a surgical probe (e.g., probe 108 of FIG. 1) that is coupled to cable 110. As described above, the interface plane of cable 110 comprises the proximal ends of the four cores of cable 110 that are exposed through an opening 217 of ferrule 215 of port adapter 114.

Once the surgeon is able to view inside the eye's globe, the surgeon may project from the distal end of the probe one or more desired aiming beam spots onto the retina. More specifically, after activation by the surgeon, laser source 206 emits aiming beam 212 onto beam splitter 218, which reflects aiming beam 212 onto diffraction optical element (DOE) 220. As further described in relation to FIG. 6, DOE 220 may comprise different diffraction segments (e.g., three segments), each configured to diffract or split a beam into a different number of beams. A diffraction segment may also be referred to as a "segment" herein. In the example of FIG. 2, DOE 220 is positioned such that aiming beam 212 is aligned with the middle segment of DOE 220, which diffracts aiming beam 212 into aiming beams (e.g., four aiming beams). However, a surgeon may change the position of DOE 220 in order to diffract a beam into a different number of beams (e.g., one or two). For example, using voice command or some other feature of surgical laser system 202, a surgeon may position DOE 220 to align aiming beam 212 with a different segment of DOE 220, which may diffract aiming beam 212 into one, two, or other numbers of beams.

Once diffracted, the resulting aiming beams are reflected by beam splitter 226 onto condensing lens 224. Condensing lens 224 then focuses the four aiming beams onto the interface plane of a proximal end of cable 110 such that each of the aiming beams is propagated, along an entire length of a corresponding core of cable 110, to the distal end of a surgical probe (e.g., probe 108 of FIG. 1). This allows the surgeon to project from the distal end of the probe four desired aiming beam spots onto the retina.

As described above, once the surgeon has positioned and activated the laser probe so as to project one or more aiming beam spots onto the retina, the surgeon may then activate laser source 204, such as through a foot pedal or other means, to treat the targeted patient anatomy (e.g., photocoagulate the desired retinal spot using the treatment beam). When activated, laser source 204 emits polarized treatment beam 210, whose polarization axis may be changed by a polarization rotator 232. For example, in some embodiments, polarization rotator 232 filters treatment beam 210 to produce a vertically-polarized treatment beam which is s-polarized relative to the plane of incidence of beam splitter 226.

A polarized treatment beam 210 may be advantageous because, in some embodiments, beam splitter 226 may have coatings that are sensitive to polarization such that, for example, an s-polarized beam may reflect off of beam splitter 226 with less broadening of the wavelength. As described above, beam splitter 226 is coated such that it allows illumination beam 214 to pass through while reflecting treatment beam 210 and aiming beam 212. Therefore, to provide the surgeon with a high quality and throughput illumination beam 214, it is advantageous to polarize treatment beam 210, which allows beam splitter 226 to isolate and reflect treatment beam 210 with a narrower band of wavelength.

Once polarized, treatment beam 210 reaches beam splitter 213, which is configured to allow a substantial portion of treatment beam 210 to pass through, while reflecting a trivial portion 231 onto sensor 223. Sensor 223 is a light sensor configured to detect whether laser source 204 is active or not. After passing through beam splitter 213, treatment beam 210 is received at beam splitter 219, which is configured to reflect treatment beam 210 onto beam splitter 218. Beam splitter 218 is configured to reflect a trivial portion 233 of treatment beam 210 onto sensor 216 while allowing a substantial portion of treatment beam 210 to pass through. Sensor 216 is a light sensor configured to detect whether treatment beam 210 has reached beam splitter 218.

As shown, linearly polarized treatment beam 210 passes through beam splitter 218 at an angle with respect to beam splitter 218 that is equal to the angle with which aiming beam 212 is reflected by beam splitter 218. Therefore, once laser source 204 is active, transmitted treatment beam 210 and reflected aiming beam 212 are combined (e.g., such that they overlay each other), creating combined beam 211, before reaching DOE 220. DOE 220 then diffracts combined beam 211 into combined beams 211a-211d. Each one of combined beams 211a-211d refers to a diffracted treatment beam and a diffracted aiming beam that overlay each other.

Combined beams 211a-211d are then received at beam splitter 226, which reflects combined beams 211a-211d onto condensing lens 224. Condensing lens 224 focuses combined beams 211a-211d onto an interface plane of the proximal end of cable 110 such that each of the combined beams 211a-211d is propagated, along an entire length of a corresponding core of cable 110, to the distal end of a surgical probe (e.g., probe 108 of FIG. 1). More specifically, in the example of FIG. 2, cable 110 is an MCF with four cores, such as cores A, B, C, and D. In such an example, condensing lens 224 focuses combined beams 211a-211d onto an interface plane of a proximal end of cable 110 such that, for example, combined beam 211a is propagated onto core A, combined beam 211b is propagated onto core B, combined beam 211c is propagated onto core C, and combined beam 211d is propagated onto core D.

In the example of FIG. 2, both aiming beam 212 and treatment beam 210 are diffracted by the same DOE 220. However, in optics, the angle at which light is diffracted by a DOE is dependent upon the light's wavelength. This is because a DOE's diffraction grating is generally configured or tuned to diffract light at a certain angle only for a given wavelength. In the example of FIG. 2, DOE 220 may be tuned to ensure that any diffracted beam with a wavelength $\lambda_1$, which is equal to the wavelength of treatment beam 210 (e.g., ~532 nanometers (nm)), is diffracted at an angle $\theta_1$ with respect to the incident beam direction. Accordingly, DOE 220 is effectively able to diffract treatment beam 210 at angle $\theta_1$ for each diffracted beam. But, because aiming beam 212 has a different wavelength $\lambda_2$ (e.g., ~635 nm), DOE 220 may diffract aiming beam 212 at angle $\theta_2$ with respect to the incident beam direction, which may be slightly different than angle $\theta_1$.

Figure 3:
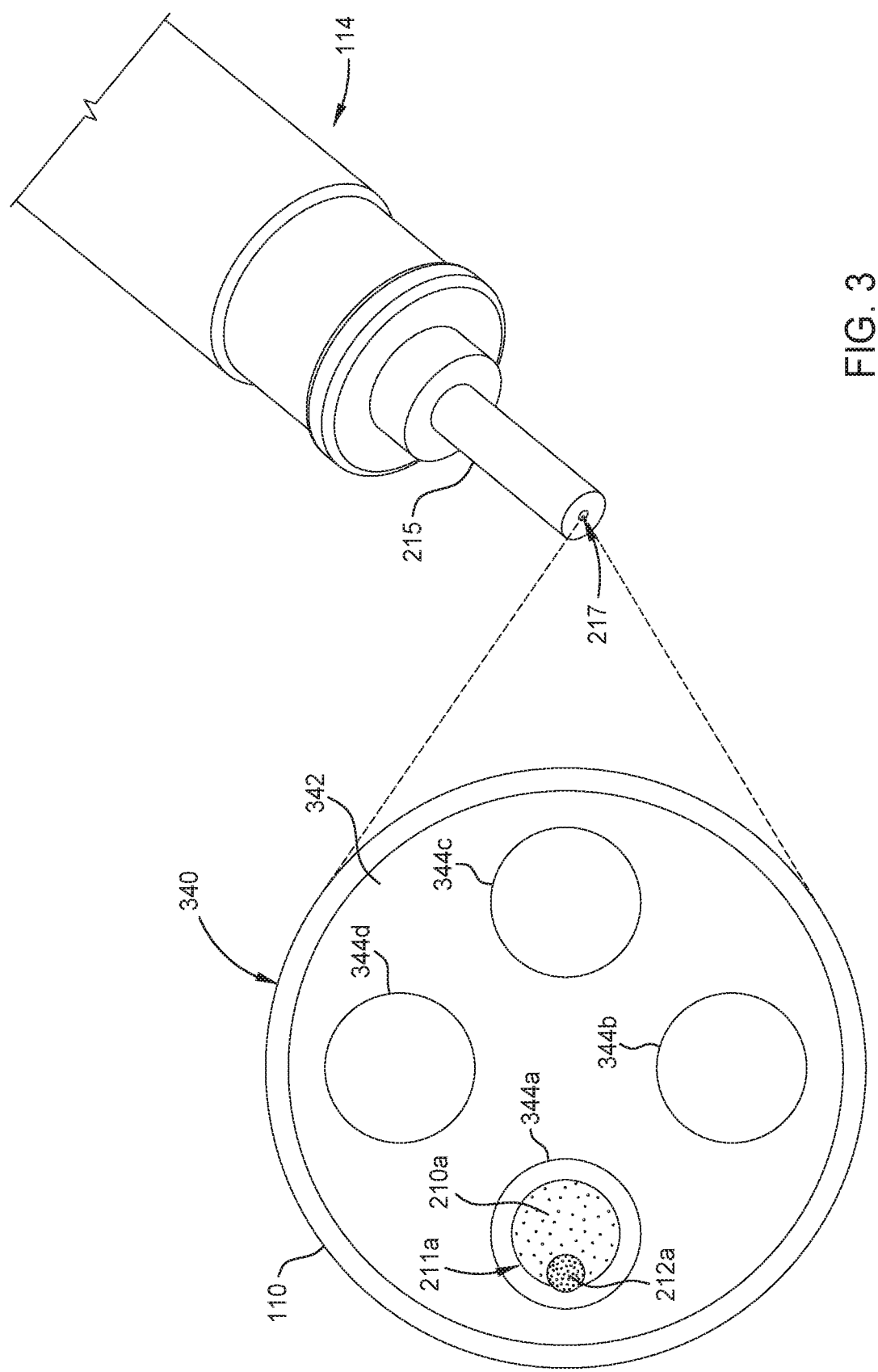
FIG. 3 illustrates an example input of the surgical laser system of FIG. 2 into an interface plane of the proximal end of a cable that is coupled to the surgical laser system, in accordance with certain aspects of the present disclosure.

Diffracting treatment beam 210 and aiming beam 212 at different diffraction angles, however, may cause a misalignment among one or more of the diffracted beams, as further shown in FIG. 3. In addition, in the example of FIG. 2, the inter-spot power non-uniformity of the major beams diffracted from DOE 220 may be minimized only for the wavelength of treatment beam 210 because the DOE grating design of DOE 220 is only optimized for treatment beam 201's wavelength. Inter-spot power non-uniformity is the maximum individual-spot power deviation from the average power of the major bear spots. DOE 220, therefore, may able to minimize the inter-spot power non-uniformity across only the four diffracted treatment beams but not across the four diffracted aiming beams. In addition, DOE 220 being only tuned to the wavelength of treatment beam 210 may result in an out-of-order leakage of aiming beam 212. In other words, DOE 220 may diffract aiming beam 212 into undesired spots, including the zero-order spot which is the portion of the incident beam that transmits, undiffracted, directly through DOE 220.

The angular deviation ($\theta_2-\theta_1$) between each diffracted beam 211a-d at the aiming beam wavelength and its corresponding diffracted beam 211a-d at the treatment wavelength is Fourier-transformed by condensing lens 224 into a spatial deviation $r_2-r_1$ of the spatial lateral position of each diffracted aiming beam 212a-d on interface plane 340 and its corresponding treatment beam 210-a-d on interface plane 340, such as in the example misalignment of FIG. 3 More specifically, FIG. 3 illustrates input into an interface plane 340 of the proximal end of cable 110, which is exposed through an opening 217 of ferrule 215. Interface plane 340, as described above, comprises the exposed proximal ends of the four cores 344a-344d of the MCF cable 110 that extend through port adapter 114. As shown, because DOE 220 diffracts treatment beam 210 and aiming beam 212 at different angles, aiming beam 212a is not aligned with the center of treatment beam 210a, which may correspond to the center of core 344a. As a result, aiming beam 212a is not centered in core 344a. Note that the other three combined beams 211b-211d are not shown in FIG. 3 for simplicity.

In the case of surgical laser system 202, the tolerance stack-up of lateral misalignments of the overall laser/probe optical system may cause one or more aiming beams 212a-d at interface plane 340 to not couple fully into its respective fiber core 334, while other aiming beams 212a-d may fully couple into their respective fiber cores. This may greatly increase the inter-spot power non-uniformity of the multiple aiming beams 212a-d projected out of the probe and focused onto the retina. As such, one or more of the aiming beam spots projected on the retina may be dim relative to the other spots, which may be irritating or distracting to the surgeon. Further, the misalignment between the treatment beam and the aiming beam significantly reduces the allowed margin for any further misalignment that may occur due to an optical drift or other types of environmental conditioning and/or perturbations. As such, any further misalignment of an already misaligned pair of treatment and aiming beams may further reduce the accuracy of the corresponding surgical laser system.

Accordingly, certain embodiments of the present disclosure relate to a surgical laser system that is configured to diffract a treatment beam and an aiming beam such that each of the diffracted aiming beams (e.g., four diffracted aiming beams) is aligned more closely with each of the corresponding diffracted treatment beams (e.g., four diffracted treatment beams).

Figure 4:
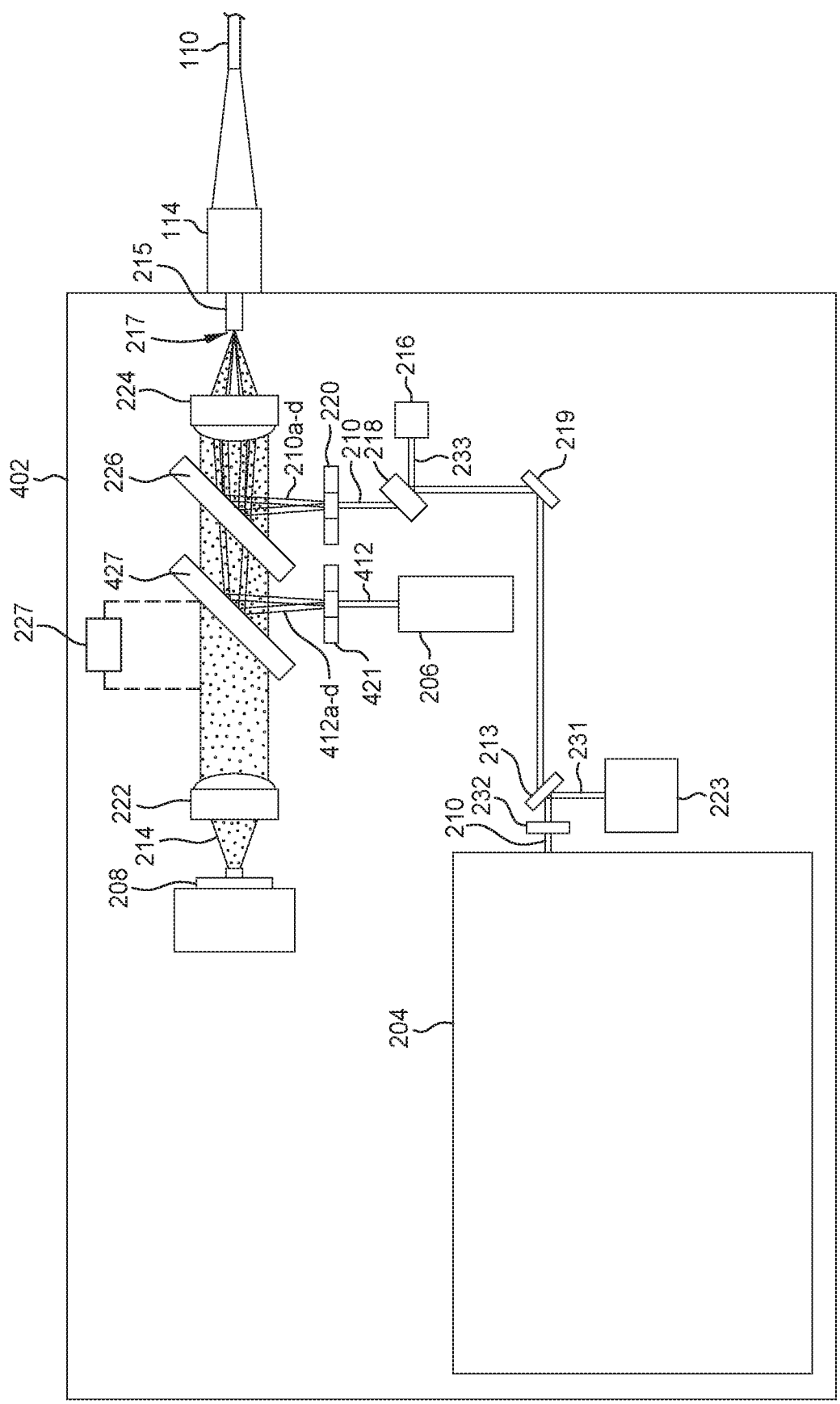
FIG. 4 illustrates an example of a surgical laser system, with two diffraction optical elements (DOEs), used for creating a multi-spot pattern of laser beams, in accordance with certain aspects of the present disclosure.

FIG. 4 illustrates an example surgical laser system 402 that may be used for creating a multi-spot pattern of combined laser beams. Surgical laser system 402 comprises a laser source 204, which generates a treatment beam 210, a laser source 206, which generates an aiming beam 412, and a light source 208, which generates an illumination beam 214. Surgical laser system 402 also comprises DOE 220, which is tuned to diffract laser beams with a wavelength of $\lambda_1$ (e.g., treatment beam 210), at an angle $\theta_1$. Surgical laser system 402 also comprises DOE 421, which is tuned to diffract laser beams with a wavelength of $\lambda_2$ (e.g., aiming beam 412), at the same angle $\theta_1$. Utilizing two DOEs allows surgical laser system 402 to diffract treatment beam 210 and aiming beam 412 both at the same angle and, thereby, ensure that the combined beams are aligned closely. As shown, surgical laser system 402 also comprises two different beam splitters 226 and 427, one to reflect beams diffracted by DOE 220 and another to reflect beams diffracted by DOE 421.

When activated by the surgeon, laser source 206 emits aiming beam 412, which is diffracted by DOE 421 at angle $\theta_1$, into aiming beams 412a-412d. Aiming beams 412a-412d then reflect off of beam splitter 427 onto condensing lens 224. As described above, beam splitter 226 is coated such that light propagated onto side 226a is able to pass through beam splitter 226. As such, aiming beams 412a-412d are able to efficiently transmit through beam splitter 226 without any change to their angular directions in the collimated-space region before lens 224, or their angles of incidence onto interface plane 340 in FIG. 5. The angle of incidence refers to an angle which an incident line or ray makes with a line perpendicular to the surface at the point of incidence. Condensing lens 224 then focuses aiming beams 412a-412d onto an interface plane of a proximal end of cable 110 such that each of the aiming beams 412a-412d is propagated, along an entire length of a corresponding core of cable 110, to the distal end of a surgical probe (e.g., probe 108 of FIG. 1).

Once the surgeon has illuminated the desired retinal spots with aiming beams 412a-412d, the surgeon activates laser source 204, which then emits treatment beam 210. Treatment beam 210 may take the same path described in relation to FIG. 2 and reach DOE 220, which is configured to diffract treatment beam 210, at the same angle $\theta_1$, into treatment beams 210a-210d. Treatment beams 210a-210d then reflect off of beam splitter 226 onto condensing lens 224, which focuses treatment beams 210a-210d onto the interface plane of the proximal end of cable 110 such that each of the treatment beams 210a-210d is propagated, along an entire length of a corresponding core of cable 110, to the distal end of a surgical probe (e.g., probe 108 of FIG. 1).

As shown in FIG. 4, because the path of treatment beam 210 is decoupled from the path of aiming beam 412 (at least before they are reflected by beam splitters 427 and 226), the diffraction angles for the two beams 210 and 412, which have different wavelengths, can be the same or even changed independent of each other. As described above, what enables this configuration is the use of two DOEs 220 and 421. As shown, both DOEs 220 and 421 are configured or positioned to diffract beams 210 and 412 into the same number of beams. In the example of FIG. 4, both DOEs 220 and 421 are positioned such that beams 210 and 412 are aligned with the middle segments of both DOEs 220 and 421, which are configured to diffract each of beams 210 and 412, respectively, into four beams. However, in some embodiments, a surgeon may cause both DOEs 220 and 421 to be repositioned such that beams 210 and 412 are diffracted into another number of diffracted beams (e.g., one or two). Repositioning DOEs 220 and 421, in some embodiments, may involve mechanically or electromechanically moving the location of DOEs 220 and 421 within surgical laser system 402. In certain embodiments, both DOEs 220 and 421 may be mounted on the same linear element (e.g., a carriage or stage (not shown)) such that by repositioning the linear element, both DOEs 220 and 421 are set to the same desired segment at the same time.

Note that, in certain embodiments, DOE 220 and 421 may instead be placed in a parallel manner with respect to each other. In such embodiments, DOE 220 and 421 are placed such that each respective segment of DOE 220 is aligned with a respective segment of DOE 421. For example, the DOE 220 and 421 may be stacked (e.g., vertically or horizontally) on top of one another. In such embodiments, DOE 220 diffracts treatment beam 210 into a number of diffracted treatment beams (e.g., one, two, four) and DOE 421 diffracts aiming beam 412 into the same number of diffracted aiming beams. Further, in such embodiments, DOE 220 and 421 would diffract treatment beam 210 and aiming beam 212, respectively, onto a single beam splitter, which then reflects the diffracted treatment beams and the diffracted aiming beams onto a condensing lens. For example, the single beam splitter may be designed to have two narrow-spectral-band high-reflectance notches, one for reflecting the diffracted treatment beams and one for reflecting the diffracted aiming beams. Further, the single beam splitter may be tall enough (e.g., vertically) to simultaneously reflect the diffracted aiming beams and the diffracted treatment beams to the condensing lens, which then focuses each of the treatment beams and its corresponding aiming beam to the interface plane of cable 110.

Figure 5:
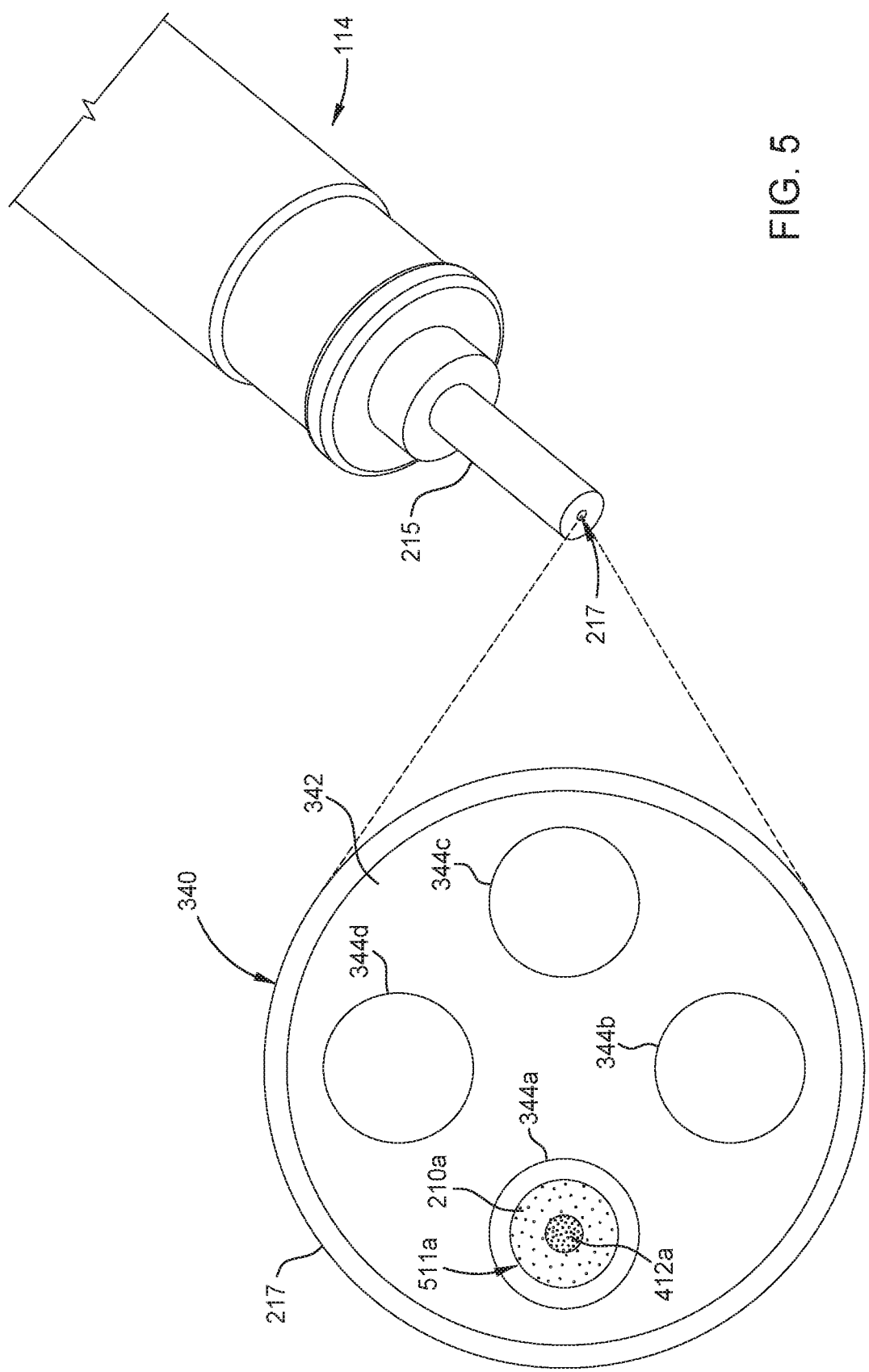
FIG. 5 illustrates an example input of the surgical laser system of FIG. 4 into an interface plane of the proximal end of a cable that is coupled to the surgical laser system, in accordance with certain aspects of the present disclosure.

FIG. 5 illustrates an example input into an interface plane 340 of the proximal end of cable 110, which is exposed through an opening 217 of ferrule 215. Because DOEs 220 and 421 are configured to diffract treatment beam 210 and aiming beam 412, respectively, at the same angle, the center of aiming beam 412*a* is now aligned with the center of treatment beam 210*a*, which may correspond to the center of core 344*a*. Note that the combination of aiming beam 412*a* and treatment beam 210*a* corresponds to combined beam 511*a*. The other three combined beams are not shown for simplicity. Because aiming beams 412*a-d* are more centered in treatment beams 210*a-d*, such as partly shown in FIG. 5, the inter-spot uniformity across the aiming beams 212*a-d* is increased. In addition, surgical laser system 402 has a higher margin for any potential misalignment that may be caused due to an optical drift or other types of environmental conditioning and/or perturbations. Also, because the inter-spot power non-uniformity of DOE 220 is minimized by optimizing its grating design for the wavelength of treatment beam 210 and the inter-spot power non-uniformity of DOE 421 is minimized by optimizing its grating design for the wavelength of aiming beam 412, the beam power uniformity across the four diffracted treatment beams and the four diffracted aiming beams can be optimized. Using DOE 421, which is tuned to the wavelength of aiming beam 412, also reduces the out-of-order leakage of aiming beam 412.

Further, surgical laser system 402 has a higher angular stability and is less prone to misalignment, as compared to surgical laser system 202, because beam splitter 218 no longer reflects aiming beam 412. Generally, alignment sensitivity is much higher for reflection than for transmission. Since beam splitter 218 of surgical laser system 402 is only used for transmission of laser beams (i.e., treatment beam 210), it is not a major source of potential beam angular stability and alignment. Because even if environmental conditioning and/or perturbations cause slight misalignments to beam splitter 218, the angle at which treatment beam 210 is transmitted may not be significantly impacted. In surgical laser system 202, however, beam splitter 218 is used for both reflection (i.e., reflection of aiming beam 212) and transmission (i.e., transmission of treatment beam 210). As such, any small misalignment of beam splitter 218 may significantly impact the angle with which aiming beam 212 is reflected. In addition, the arrangement of components in surgical laser system 402, allows for a more optimal placement of sensor 227. As shown in FIG. 5, sensor 227 is placed such that it is less likely to receive any scattered light from treatment beam 210. Sensor 227 may be sensitive to green light (e.g., treatment beam 210) when attempting to sense the presence of white light (e.g., illumination beam 214) and, therefore, by receiving scattered light from treatment beam 210, sensor 227 may mistakenly determine the presence of illumination beam 214. For example, the placement of sensor 227 in surgical laser system 202 is such that it may receive some of the scattered light from the diffracted treatment beams 210*a-d* and incorrectly detect the presence of illumination beam 214.

Figure 6:
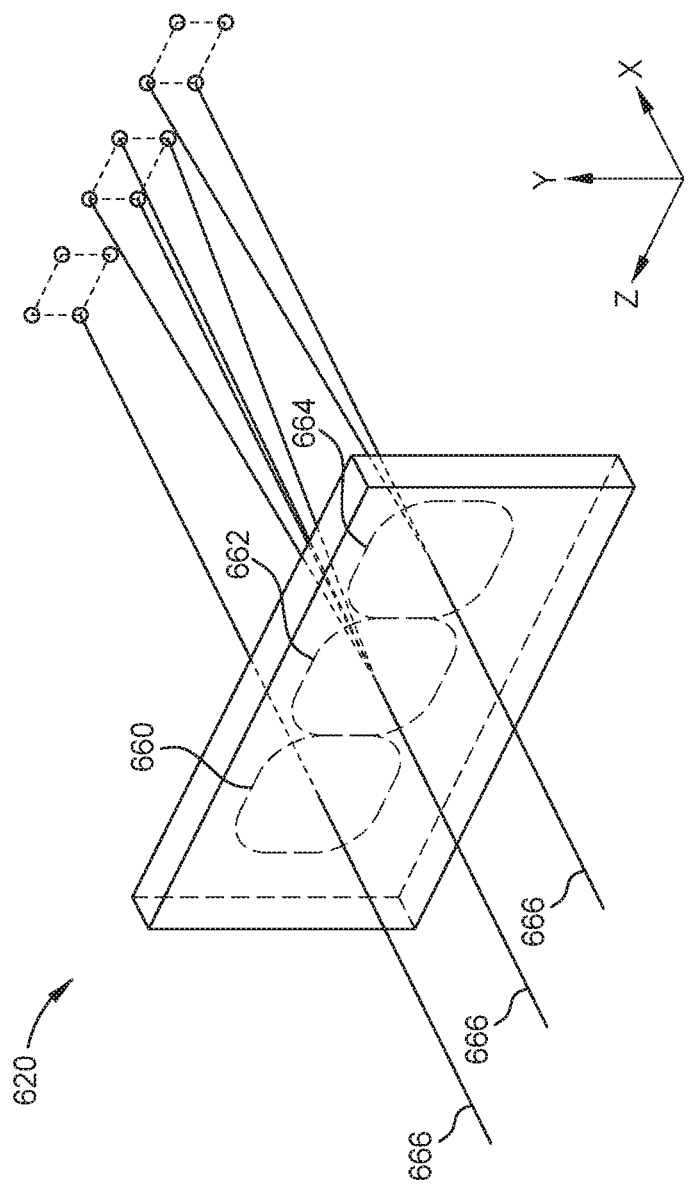
FIG. 6 illustrates an example DOE having three segments, in accordance with certain aspects of the present disclosure.

FIG. 6 illustrates an example DOE 620 having three segments 660, 662, and 664. DOE 620 is similar to DOEs 220 and 421 in terms of the number of segments it has. As shown, a beam 666 is diffracted by segment 660 into one beam while the same beam 666 is diffracted by segment 662 into four beams. Segment 664 diffracts beam 666 into two beams.

A user, such as a surgeon, may select a desired number of beams to be propagated from a probe. For example, the surgeon may select four treatment beams to be propagated from the probe. The surgeon's selection is received at the surgical laser system (e.g., surgical laser system 102, 202, or 402) as input into the system's central processing unit (CPU). The CPU may then be configured to execute a certain set of instructions that are stored in the system's memory, which cause the system to position the system's DOE(s) based on the surgeon's selection. In the example of DOEs 421 and 220, the processor may cause an electromechanical motor to move a carriage on which DOEs 421 and 220 are mounted to ensure that aiming beam 212 and treatment beam 210 are aligned with segments of DOEs 421 and 220, respectively, that are configured to diffract the beams into four diffracted beams.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:
1. A surgical laser system, comprising:
a first laser source configured to emit a first laser beam with a first wavelength;
a second laser source configured to emit a second laser beam with a second wavelength,
a first diffraction optical element (DOE) tuned to the first wavelength, wherein the first DOE is configured to diffract the first laser beam into one or more first diffracted beams at a diffraction angle, wherein the first DOE comprises two or more different diffraction segments each configured to diffract the first laser beam into a different number of beams depending on which diffraction segment the first laser beam passes through;
a second DOE tuned to the second wavelength, wherein the second DOE is configured to diffract the second laser beam into one or more second diffracted beams at the diffraction angle, wherein the second DOE comprises two or more different diffraction segments each configured to diffract the second laser beam into a different number of beams depending on which diffraction segment the second laser beam passes through;
wherein the first DOE and the second DOE are coupled together, wherein the first DOE and the second DOE are configured to move together such that the first laser beam and the second laser beam pass through respective diffraction segments in the first DOE and the second DOE that will split the first laser beam and the second laser beam into a same number of respective beams;
a first and second beam splitter; and
a lens;
a light source configured to emit an illumination beam onto the lens, wherein once emitted b the light source the illumination beam passes through the first beam splitter and the second beam splitter;
a cable;
wherein the first beam splitter is configured to reflect the one or more first diffracted beams onto the lens and wherein the second beam splitter is configured to reflect the one or more second diffracted beams onto the lens,
wherein once reflected by the second beam splitter, the one or more second diffracted beams pass through the first beam splitter before reaching the lens; and
wherein the lens is configured to focus the illumination beam, the one or more first diffracted beams, and the one or more second diffracted beams onto an interface plane of a proximal end of the cable, wherein a distal end of the cable is configured to project the illumination beam, one or more first diffracted beams, and the one or more second diffracted beams onto a target surface.

2. The surgical laser system of claim 1, wherein:
the cable is a multi-core optical fiber (MCF) with multiple cores;
wherein the lens is configured to focus a first one of the one or more first diffracted beams on a first one of the multiple cores;
wherein the lens is configured to focus a first one of the one or more second diffracted beams on the first one of the multiple cores; and
wherein the lens is configured to align a center of the first one of the one or more first diffracted beams with a center of the first one of the one or more second diffracted beams.

3. The surgical laser system of claim 2, wherein the lens is configured to align the center of the first one of the one or more first diffracted beams and the center of the first one of the one or more second diffracted beams with a center of the first one of the multiple cores.

\* \* \* \* \*